United States Patent [19]

Arnett

[11] Patent Number: 5,651,772

[45] Date of Patent: Jul. 29, 1997

[54] NEEDLE GUARD ASSEMBLY

[75] Inventor: Jeffery D. Arnett, Ypsilanti, Mich.

[73] Assignee: Aeroquip Corporation, Maumee, Ohio

[21] Appl. No.: 608,050

[22] Filed: Feb. 28, 1996

[51] Int. Cl.$^6$ ............................................. A61M 5/178
[52] U.S. Cl. ........................... 604/164; 604/165; 604/198
[58] Field of Search ...................................... 604/164, 165, 604/166, 167, 198

[56] References Cited

U.S. PATENT DOCUMENTS

| | | | |
|---|---|---|---|
| 4,211,741 | 7/1980 | Ostoich | 264/173 |
| 4,391,029 | 7/1983 | Czuba et al. | 29/450 |
| 4,424,833 | 1/1984 | Spector et al. | 137/849 |
| 4,588,398 | 5/1986 | Daugherty et al. | 604/265 |
| 4,661,300 | 4/1987 | Daugherty | 264/40.6 |
| 4,664,657 | 5/1987 | Williamitis et al. | 604/265 |
| 4,683,916 | 8/1987 | Raines | 137/854 |
| 4,713,057 | 12/1987 | Huttner et al. | 604/164 |
| 4,728,322 | 3/1988 | Walker et al. | 604/165 |
| 4,781,703 | 11/1988 | Walker et al. | 604/264 |
| 4,832,696 | 5/1989 | Luther et al. | 604/164 |
| 4,846,805 | 7/1989 | Sitar | 604/165 |
| 4,850,961 | 7/1989 | Wanderer et al. | 604/164 X |
| 4,883,699 | 11/1989 | Aniuk et al. | 428/36.9 |
| 4,917,669 | 4/1990 | Bonaldo | 604/164 |
| 4,944,728 | 7/1990 | Carrell et al. | 604/164 |
| 4,952,207 | 8/1990 | Lemieux | 604/164 |
| 5,000,740 | 3/1991 | Ducharme et al. | 604/162 |
| 5,013,304 | 5/1991 | Russell et al. | 604/167 |
| 5,019,049 | 5/1991 | Haining et al. | 604/165 |
| 5,051,109 | 9/1991 | Simon | 604/263 |
| 5,088,985 | 2/1992 | Deras | 604/192 |
| 5,088,986 | 2/1992 | Nusbaum | 604/195 |
| 5,088,987 | 2/1992 | Noonan, Jr. | 604/195 |
| 5,088,988 | 2/1992 | Talonn et al. | 604/164 |
| 5,092,845 | 3/1992 | Chang | 604/164 |
| 5,092,853 | 3/1992 | Couvertier, II | 604/195 |
| 5,102,394 | 4/1992 | Lasaitis et al. | 604/164 |
| 5,108,374 | 4/1992 | Lemieux | 604/164 |
| 5,127,905 | 7/1992 | Lemieux | 604/164 |
| 5,135,504 | 8/1992 | McLees | 604/164 |
| 5,171,231 | 12/1992 | Heiliger | 604/164 X |
| 5,176,650 | 1/1993 | Haining | 604/164 |
| 5,183,469 | 2/1993 | Capaccio | 604/192 |
| 5,188,597 | 2/1993 | Sweeney et al. | 604/110 |
| 5,188,607 | 2/1993 | Wu | 604/167 |
| 5,201,713 | 4/1993 | Rosetti | 604/165 |
| 5,215,525 | 6/1993 | Sturman | 604/164 |
| 5,215,527 | 6/1993 | Beck et al. | 604/164 |
| 5,215,528 | 6/1993 | Purdy et al. | 604/164 |
| 5,219,333 | 6/1993 | Sagstetter et al. | 604/198 X |
| 5,226,899 | 7/1993 | Lee et al. | 604/282 |
| 5,234,416 | 8/1993 | Macaulay et al. | 604/282 |
| 5,240,537 | 8/1993 | Bodicky | 156/244.13 |
| 5,242,393 | 9/1993 | Brimhall et al. | 604/86 |
| 5,250,034 | 10/1993 | Appling et al. | 604/164 |
| 5,250,066 | 10/1993 | Lambert | 606/181 |
| 5,254,107 | 10/1993 | Soltesz | 604/282 |
| 5,261,885 | 11/1993 | Lui | 604/247 |
| 5,267,971 | 12/1993 | Brimhall | 604/177 |
| 5,267,979 | 12/1993 | Appling et al. | 604/247 |
| 5,273,543 | 12/1993 | Bell et al. | 604/110 |
| 5,279,590 | 1/1994 | Sinko et al. | 604/198 X |
| 5,279,591 | 1/1994 | Simon | 604/263 |
| 5,300,048 | 4/1994 | Drewes, Jr. et al. | 604/280 |
| 5,304,136 | 4/1994 | Erskine et al. | 604/110 |
| 5,304,140 | 4/1994 | Kugo et al. | 604/281 |
| 5,304,144 | 4/1994 | Brimhall | 604/177 |
| 5,304,149 | 4/1994 | Morigi | 604/192 |
| 5,304,155 | 4/1994 | Lui | 604/247 |
| 5,306,253 | 4/1994 | Brimhall | 604/165 |
| 5,308,330 | 5/1994 | Grimard | 604/110 |
| 5,312,361 | 5/1994 | Zadini et al. | 604/165 |
| 5,312,371 | 5/1994 | Dombrowski et al. | 604/198 |
| 5,316,706 | 5/1994 | Muni et al. | 264/25 |

(List continued on next page.)

*Primary Examiner*—Sam Rimell
*Assistant Examiner*—Robert V. Racunas
*Attorney, Agent, or Firm*—Emch, Schaffer, Schaub & Porcello Co., L.P.A.

[57] ABSTRACT

The present invention is directed to a needle guard assembly including a needle, a body and a handle. The body defines a chamber for receiving the needle. The handle moves the needle from the exterior of the body into the chamber.

7 Claims, 3 Drawing Sheets

U.S. PATENT DOCUMENTS

| | | | |
|---|---|---|---|
| 5,328,473 | 7/1994 | Fayngold et al. | 604/110 |
| 5,334,144 | 8/1994 | Alchas et al. | 604/68 |
| 5,338,310 | 8/1994 | Lewandowski | 604/192 |
| 5,342,309 | 8/1994 | Hausser | 604/110 |
| 5,344,404 | 9/1994 | Benson | 604/110 |
| 5,344,408 | 9/1994 | Partika | 604/192 |
| 5,356,390 | 10/1994 | Erskine | 604/164 |
| 5,370,624 | 12/1994 | Edwards et al. | 604/169 |
| 5,376,073 | 12/1994 | Graves et al. | 604/86 |
| 5,380,298 | 1/1995 | Zabetakis et al. | 604/265 |
| 5,380,307 | 1/1995 | Chee et al. | 604/264 |
| 5,385,554 | 1/1995 | Brimhall | 604/168 |
| 5,385,555 | 1/1995 | Hausser | 604/192 |
| 5,395,341 | 3/1995 | Slater | 604/164 |
| 5,397,512 | 3/1995 | Sloane, Jr. et al. | 264/25 |
| 5,405,323 | 4/1995 | Rogers et al. | 604/53 |
| 5,407,431 | 4/1995 | Botich et al. | 604/110 |
| 5,409,461 | 4/1995 | Steinman | 604/110 |
| 5,409,463 | 4/1995 | Thomas et al. | 604/167 |
| 5,409,644 | 4/1995 | Martin et al. | 264/25 |
| 5,411,486 | 5/1995 | Zadini et al. | 604/198 |
| 5,415,184 | 5/1995 | Peck | 128/880 |
| 5,417,668 | 5/1995 | Setzer et al. | 604/263 |
| 5,419,766 | 5/1995 | Chang et al. | 604/110 |
| 5,419,777 | 5/1995 | Hofling | 604/264 |
| 5,423,766 | 6/1995 | Di Cesare | 604/192 |
| 5,423,773 | 6/1995 | Jimenez | 604/282 |
| 5,425,712 | 6/1995 | Goodin | 604/96 |
| 5,425,735 | 6/1995 | Rosen et al. | 606/128 |
| 5,425,903 | 6/1995 | Sloane, Jr. et al. | 264/22 |
| 5,429,613 | 7/1995 | D'Amico | 604/198 |
| 5,429,617 | 7/1995 | Hammersmark et al. | 604/264 |
| 5,435,314 | 7/1995 | Dias | 128/662.06 |
| 5,437,648 | 8/1995 | Graves et al. | 604/263 |
| 5,441,489 | 8/1995 | Utsumi et al. | 604/280 |
| 5,443,457 | 8/1995 | Ginn et al. | 604/280 |
| 5,445,619 | 8/1995 | Burns | 604/192 |
| 5,445,624 | 8/1995 | Jimenez | 604/280 |
| 5,446,230 | 8/1995 | Travers et al. | 585/748 |
| 5,447,501 | 9/1995 | Karlsson et al. | 604/198 |
| 5,447,503 | 9/1995 | Miller | 604/280 |
| 5,447,724 | 9/1995 | Helmus et al. | 424/426 |
| 5,449,349 | 9/1995 | Sallee et al. | 604/180 |
| 5,453,095 | 9/1995 | Davila et al. | 604/167 |
| 5,453,099 | 9/1995 | Lee et al. | 604/282 |
| 5,456,668 | 10/1995 | Ogle, II | 604/110 |
| 5,456,674 | 10/1995 | Bos et al. | 604/280 |
| 5,458,658 | 10/1995 | Sircom | 604/192 |
| 5,462,533 | 10/1995 | Daugherty | 604/164 |
| 5,464,398 | 11/1995 | Haindl | 604/280 |
| 5,464,399 | 11/1995 | Boettger | 604/283 |
| 5,472,430 | 12/1995 | Vaillancourt et al. | 604/198 |
| 5,474,539 | 12/1995 | Costa et al. | 604/164 |
| 5,478,313 | 12/1995 | White | 604/110 |
| 5,478,328 | 12/1995 | Silverman et al. | 604/272 |
| 5,520,654 | 5/1996 | Wahlberg | 604/164 |
| 5,531,701 | 7/1996 | Luther | 604/165 |
| 5,562,631 | 10/1996 | Bogert | 604/164 |

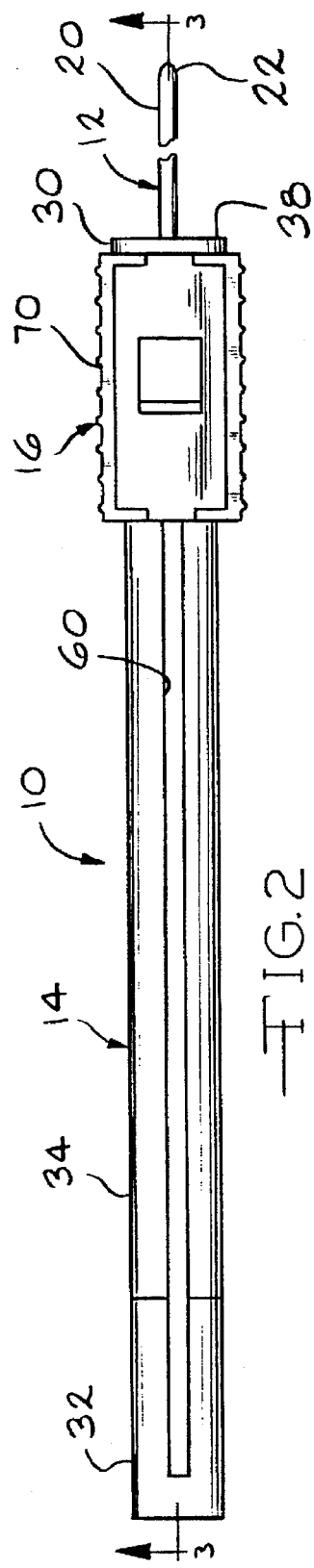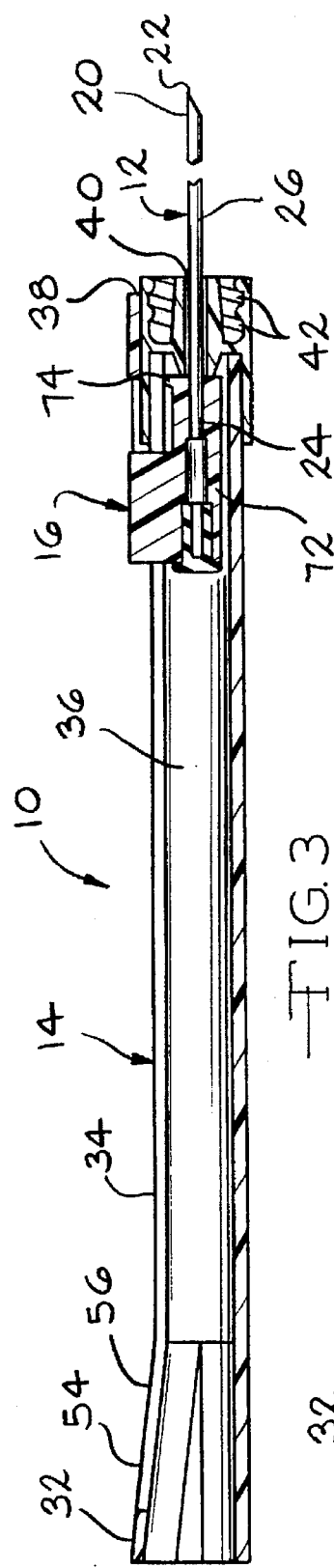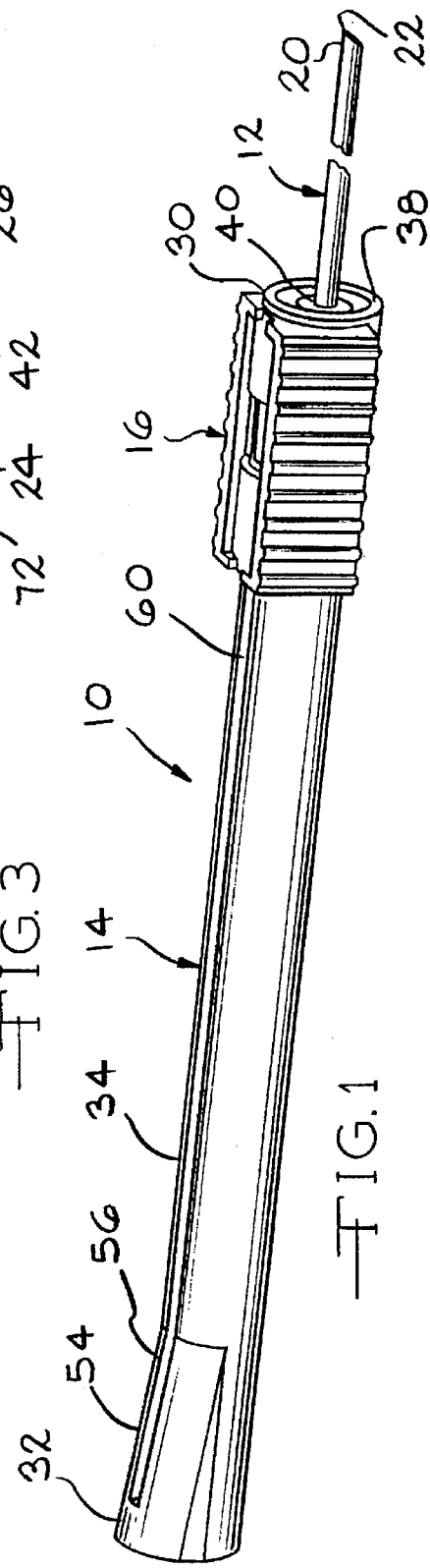

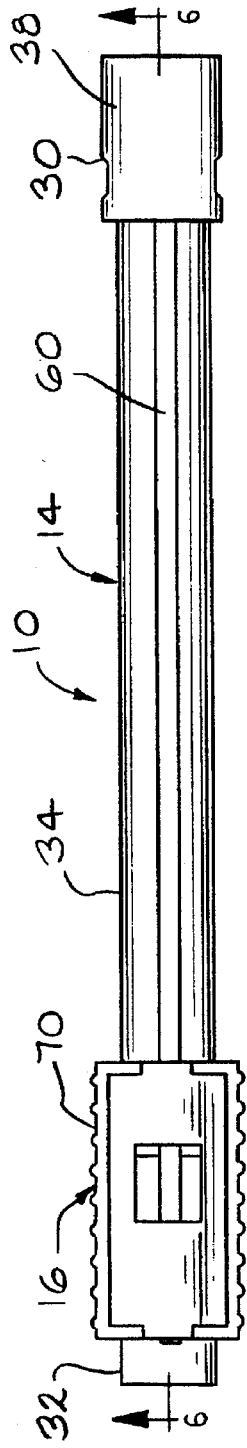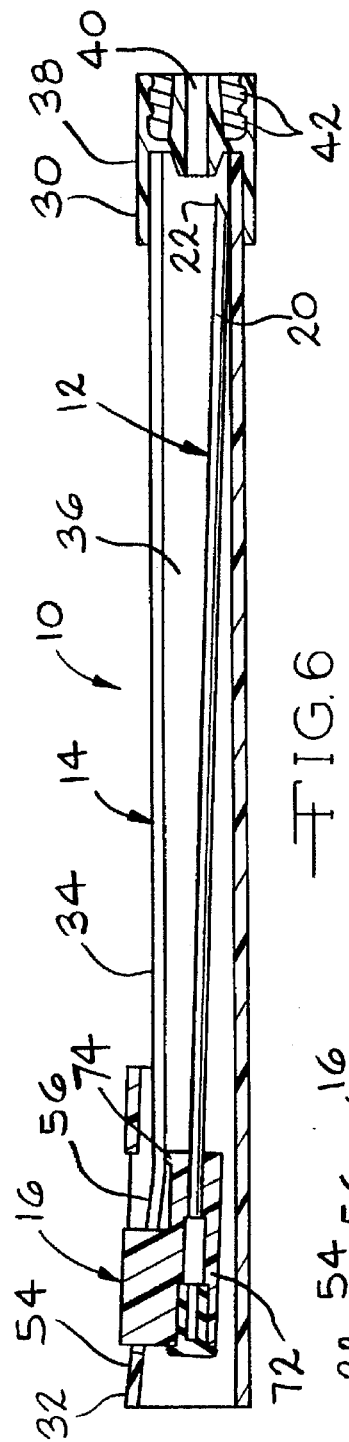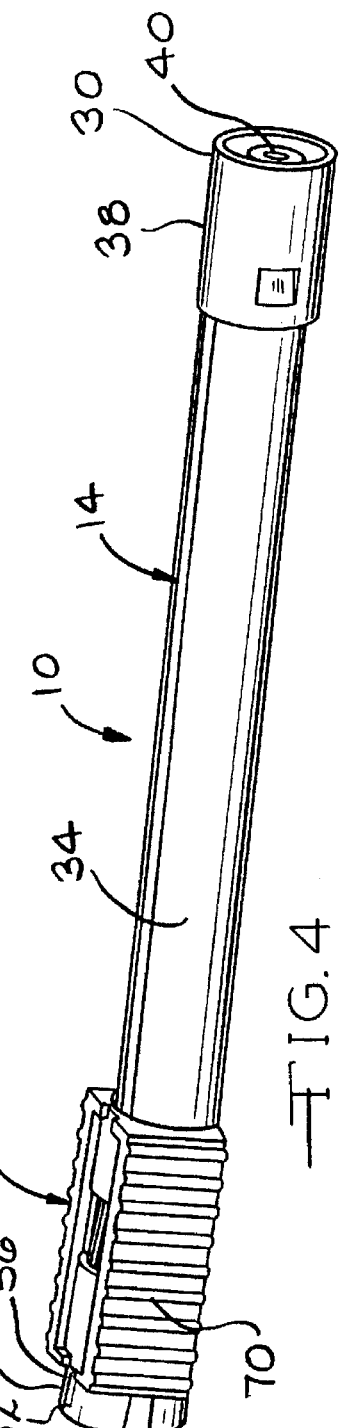

NEEDLE GUARD ASSEMBLY

BACKGROUND OF THE INVENTION

The present invention relates to a needle guard assembly. More specifically, the invention is directed to a needle guard assembly having a body that defines a chamber. A handle, which is in communication with the needle, can cause the needle to be retracted from the exterior of the body into the chamber. When the needle is fully retracted, the pointed end of the needle is contained within the chamber.

It has been determined that certain viruses such as the hepatitis B virus can be transmitted from one person to another by accidental "needle-pokes". This type of accident can happen during medical procedures. An example of such a procedure is the insertion of a catheter in a blood vessel with a needle. After the catheter has been inserted in the blood vessel, the needle is removed from the cannula of the catheter at which time the pointed end of the needle can be accidentally poked into the person handling the needle or someone in the vicinity of the needle. The residual blood on the needle can be inserted in the person poked by the needle thereby transmitting a virus in the blood.

It has been found that there is a need for a needle guard assembly in which the needle can be easily handled during insertion in a person and then retracted into the handle so that the pointed end of the needle cannot come into contact with another person. The present invention satisfies this need.

SUMMARY OF THE INVENTION

The present invention is directed to a needle guard assembly having a needle, a body and a handle in communication with the needle. The body defines a chamber for receiving the needle. The handle is movably mounted on the body. When the handle is moved, the needle is moved from the exterior of the body into the chamber defined by the body. The needle is fully retracted into the chamber so that the pointed end of the needle cannot contact a person.

It is the primary object of the present invention to provide a needle guard assembly that retracts a needle from the exterior of the assembly into the assembly to prevent accidental needle-pokes.

Other objects and advantages of the invention shall become apparent to those skilled in the art upon a review of the following detailed description of the preferred embodiment and the accompanying drawings.

BRIEF DESCRIPTION OF THE DRAWINGS

FIG. 1 is a perspective view of the needle guard assembly according to the present invention;

FIG. 2 is a top plan view of the needle guard assembly of the present invention showing the needle, the body and the handle;

FIG. 3 is a cross sectional view taken through line 3—3 of FIG. 2;

FIG. 4 is a perspective view similar to the view of FIG. 1 showing the needle fully retracted into the body;

FIG. 5 is a view similar to the view of FIG. 2 showing the needle fully retracted into the body;

FIG. 6 is a cross sectional view taken through line 6—6 of FIG. 5; and

DETAILED DESCRIPTION OF THE PREFERRED EMBODIMENT

Figure 7:
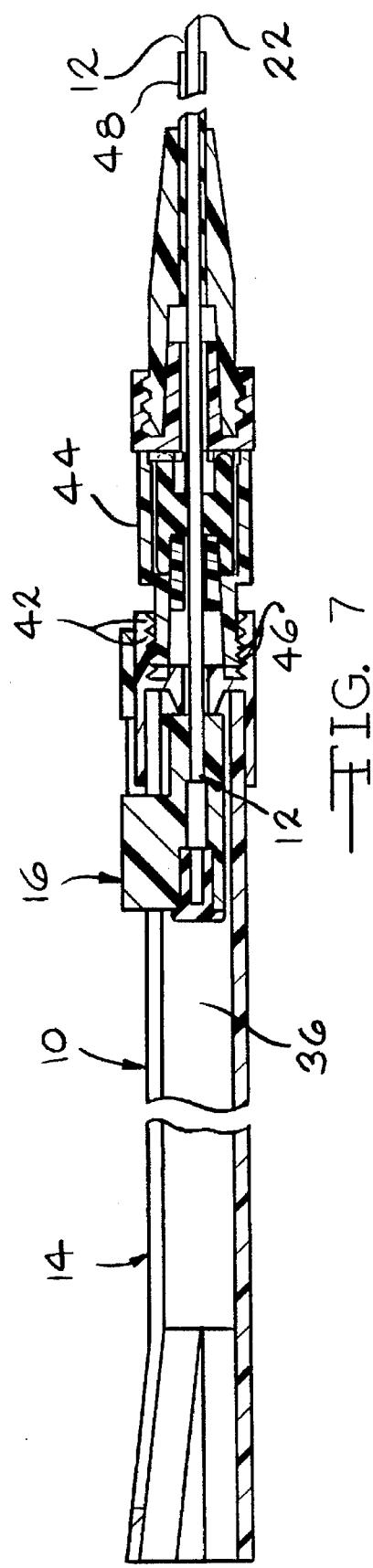
FIG. 7 is a cross sectional view taken through the center of the needle guard assembly according to the present invention and a catheter valve assembly to which the present invention is attached.

The preferred embodiment and best mode of the present invention will now be described in detailed with reference being made to the drawings. The needle guard assembly of the present invention is indicated generally in the drawings by the reference number "10". The assembly 10 includes a needle 12, a body 14 and a handle 16.

Referring to FIGS. 1 through 3, the needle 12 includes a pointed end 20 having a point 22 and an opposed handle end 24 that is connected to the handle 16. As shown in FIG. 3, a needle passageway 26 extends from the pointed end 20 to the handle end 24. The needle 12 can be made from a variety of materials, with metal being preferred. The needle 12 can include a variety of shapes and lengths.

Still referring to FIGS. 1 through 3, the body 14 includes a first end 30 and a second end 32. A side wall 34 extends longitudinally between the first and second ends 30 and 32. The side wall 34 defines a chamber 36 for receiving the needle 12. The chamber 36 should be of sufficient length to accommodate the entire length of the needle 12.

As shown in FIG. 3, the first end 30 of the body 14 includes an end cap 38. A needle opening 40 is defined by the end cap 38. When the needle 12 is extended, the needle is positioned in the needle opening 40. The end cap 38 includes threads 42 for attaching the end cap 38 and thus the body 14 to an appliance. An example of an appliance that can be attached to the end cap 38 is a valve assembly 44 as shown in FIG. 7. The valve assembly 44 includes threads 46 that mate with the threads 42 of the end cap 38. The valve assembly 44 includes, among other things, a catheter 48 through which the needle 12 extends for the insertion of the catheter 48 into a blood vessel. It should be understood that the assembly 10 of the present invention can be used with appliances other than the one shown in FIG. 7. As shown in FIGS. 1 and 3, the second end 32 of the body 14 includes a ramp 54 having an inclined surface 56. As shown in FIGS. I and 2, the side wall 34 of the body 14 defines a slot 60 that extends between the first end 30 and the second end 32.

Referring to FIGS. 1 through 3, the handle 16 of the assembly 10 includes a gripping member 70 and a needle hub 72. The gripping member 70 surrounds the exterior surface of the body 14. The needle hub 72 is positioned in the chamber 36. In the present embodiment, the gripping member 70 is directly attached to the needle hub 72. Referring to FIG. 3, the needle hub 72 defines a foot 74 that travels along the slot 60 of the body 14. As shown in FIG. 3, the handle end 24 of the needle 12 is attached to the needle hub 72. Movement of the gripping member 70 results in movement of the needle 12. The body 14, the end cap 38 and the handle 16 can be made of a variety of materials, with plastic being preferred.

The use of the assembly 10 will now be described. Referring to FIGS. 1 and 4 through 6, when the handle 16 is positioned adjacent the first end 30 of the body 14, a portion of the needle 12 is positioned outside the body. When the needle 12 is to be retracted into the body 14, the person operating the assembly 10 grips the gripping member 70 and pulls the handle 16 from the first end 30 toward the second end 32 of the body 14. The handle 16 travels along the slot 60. This causes the needle 12 to enter the chamber 36 of the body 14. When the handle 16 is adjacent the second end 32, the pointed end 20 enters the needle opening 40 and then enters the chamber 36. As shown in FIG. 6, the foot 74 of the handle 16 moves up the inclined surface 56 of the ramp 54 allowing the handle 16 to twist with respect to the body 14. This causes the needle 12 to be misaligned with the needle opening 40 thus preventing the pointed end 20 of the needle 12 from entering the needle opening 40 so that the needle can exit to the exterior of the body 14. After retraction of the needle 12 into the body 14, the assembly 10 can be discarded.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. A needle guard assembly comprising:

a needle having a pointed end and an opposed handle end;

a body having a first end and a second end, said body including a side wall extending longitudinally between said first and second ends, said side wall defining a chamber for receiving said needle, said first end defining a needle opening for receiving said needle, said second end including a ramp having an inclined surface, said side wall defining a slot extending between said first end and said second end; and a handle having a gripping member in communication with a needle hub, said needle hub being attached to said handle end of said needle, said needle hub defining a foot being received by said slot, whereby movement of said handle from said first end to said second end causes corresponding movement of said needle through said needle opening into said chamber, during such movement said foot travels along said slot until said foot moves up said inclined surface of said ramp to allow said handle to twist with respect to said body thereby causing said needle to become misaligned with said needle opening to prevent said pointed end of said needle from exiting said chamber through said needle opening.

2. The invention of claim 1, wherein a needle passageway extends from said pointed end to said handle end.

3. The invention of claim 1, wherein said first end includes an end cap.

4. The invention claim 3, wherein said end cap defines said needle opening for receiving said needle.

5. The invention of claim 3, wherein said end cap includes attachment means to attach said body to an appliance.

6. The invention of claim 5, wherein said attachment means includes threads.

7. The invention of claim 5, wherein said appliance is a valve assembly having a catheter through which needle extends for insertion of said catheter into a blood vessel.

* * * * *